US00PP11759P2

(12) United States Plant Patent
Bergman

(10) Patent No.: US PP11,759 P2
(45) Date of Patent: Jan. 30, 2001

(54) HIBISCUS PLANT NAMED 'CANDY WIND'

(75) Inventor: Wendy R. Bergman, Lehigh Acres, FL (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/333,130

(22) Filed: Jun. 14, 1999

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Candy Wind', characterized by its glossy, undulate, dark green leaves; upright, outwardly spreading, uniform, dense and symmetrical plant habit that is appropriate for container production; very freely flowering; numerous large pink-colored flowers with large dark red "eyes"; good resistance to flower bud abscission; and excellent postproduction longevity.

2 Drawing Sheets

BACKGROUND OF THE INVENTION

The present invention relates to a new and distinct cultivar of Hibiscus, botanically known as *Hibiscus rosa-sinensis*, and hereinafter referred to by the cultivar name Candy Wind.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, resistance to flower bud abscission, and good postproduction longevity.

The new Hibiscus originated from a cross made by the Inventor in Alva, Fla., of a proprietary *Hibiscus rosa-sinensis* selection, designated as code No. YB-1242, as the female, or seed, parent with the *Hibiscus rosa-sinensis* cultivar Pink Versicolor, not patented, as the male, or pollen, parent. The cultivar Candy Wind was discovered and selected by the Inventor as a flowering plant within the progeny of the stated cross in a controlled environment in Alva, Fla., on Sep. 13, 1995.

Compared to plants of the white-flowered female parent, the proprietary Hibiscus selection code No. YB-1242, plants of the new Hibiscus have darker green foliage and flowers that are typically about 2.5 to 3.75 cm larger in diameter. Plants of new Hibiscus have slightly lighter green foliage; lighter pink flower color; and flower about two to four days earlier than plants of the male parent, the cultivar Pink Versicolor. In addition, leaf margins of plants of the new Hibiscus are crenate whereas leaf margins of plants of the cultivar Pink Versicolor are pinnatisect to incised.

Asexual reproduction of the new Hibiscus by terminal cuttings taken in a controlled environment in Alva, Fla., has shown that the unique features of this new Hibiscus are stable and reproduced true to type in successive generations.

SUMMARY OF THE INVENTION

The cultivar Candy Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Candy Wind'. These characteristics in combination distinguish 'Candy Wind' as a new and distinct cultivar:

1. Glossy, undulate, dark green leaves.
2. Upright, outwardly spreading, uniform, dense and symmetrical plant habit that is appropriate for container production.
3. Very freely flowERing, numerous large pink-colored flowers with large dark red "eyes".
4. Good resistance to flower bud abscission.
5. Excellent postproduction longevity.

Plants of the new Hibiscus can be compared to plants of the cultivar Bimini Breeze, disclosed in U.S. Plant Pat. No. 10,582. However, in side-by side comparisons conducted in Alva, Fla., plants of the new Hibiscus differ from plants of the cultivar Bimini Breeze in the following characteristics:

1. Plants of the new Hibiscus have lighter green foliage than plants of the cultivar Bimini Breeze.
2. Plants of the new Hibiscus have larger flowers, about 2.5 to 3.75 cm larger in diameter, than plants of the cultivar Bimini Breeze.
3. Flowers of plants of the new Hibiscus are flatter than flowers of plants of the cultivar Bimini Breeze.
4. Flowers of plants of the new Hibiscus have larger and more pronounced dark red "eyes" than plants of the cultivar Bimini Breeze.

BRIEF DESCRIPTION OF THE PHOTOGRAPHS

The accompanying colored photographs illustrated the overall appearance of the new Hibiscus, showing the colors as true as it is reasonably possible to obtain in colored reproductions of this type.

The photograph on the first sheet comprises a side perspective view of a typical plant of 'Candy Wind'.

The photograph on the second sheet comprises a close-up view of a typical flower of 'Candy Wind'. Both photographs were taken when plants were about 7 months old. Flower and foliage colors in the photographs may appear different from the actual colors due to light reflectance.

DETAILED BOTANICAL DESCRIPTION

The following observations, measurements and values describe plants grown in Alva, Fla., with five plants per 16.5-cm containers in polyethylene- covered greenhouses, during the late spring under conditions which closely approximate commercial production. Night temperatures ranged between 13 to 24 degrees centigrade. Day temperatures ranged between 21 and 32 degrees centigrade. Plants were about 7 months old when descriptions were taken. In the description, color references are made to The Royal Horticultural Society Colour Chart except where general terms of ordinary dictionary significance are used.

Botanical classification: *Hibiscus rosa-sinensis* cultivar Candy Wind.

Parentage:

*Female or seed parent.*—*Hibiscus rosa-sinensis* proprietary selection designated as code No. YB-1242.

*Male or pollen parent.*—*Hibiscus rosa-sinensis* cultivar Pink Versicolor, not patented.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, uniform, dense and symmetrical plant habit. Relatively vigorous.

*Branching habit.*—Freely branching, usually about four lateral branches develop after removal of terminal apex.

*Plant height, soil level to top of flowers.*—About 32 cm.

*Plant diameter, area of spread.*—About 46 cm.

*Lateral branch description.*—Length: About 26.5 cm. Diameter: About 7 mm. Texture: Immature, smooth; mature, woody and rough. Color: Immature: Brown, 200A to 200B, with green, close to 146A, at nodes. Mature: Mostly gray, 195A to 197A to 197B, with dark brown, 200A.

Foliage description:

*Arrangement.*—Alternate, single; numerous, symmetrical.

*Length.*—About 9.25 cm.

*Width.*—About 8.5 cm.

*Shape.*—Broadly ovate.

*Apex.*—Acute.

*Base.*—Obtuse to slightly cordate.

*Margin.*—Crenate.

*Aspect.*—Undulate.

*Texture.*—Glabrous and glossy on both surfaces.

*Color.*—Young foliage, upper surface: Greener than 147A. Young foliage, lower surface: Color to 146A. Mature foliage, upper surface: Darker than 147A. Mature foliage, lower surface: Darker than 147B.

*Petiole.*—Length: About 3.1 cm. Diameter: About 2.75 mm. Texture: Mostly smooth with very fine pubescence on upper surface. Color: Green undertones dominated by dark brown, 200A.

Flower description:

*Natural flowering season.*—Usually spring and summer oo during periods of warm weather.

*Flower arrangement.*—Flowers arranged singly at terminal leaf axils. Very freely flowering with usually about four flower buds and/or open flowers per terminal apex. Flowers flat and face upright to outward.

*Flower appearanc.*—Rounded, pink-colored petals with relatively large dark red "eye" or throat. Flowers are open for about one day before closing. Flowers persistent.

*Flower diameter.*—Very large, about 15.5 cm.

*Flower bud (just before showing color).*—Rate of opening: About one or two days depending on temperatures. Length: About 3.2 cm. Diameter: About 1.3 cm. Shape: Elliptic.

*Petals.*—Texture: Crepe, slightly ruffled. Arrangement: Corolla consists of five petals that overlap. Shape: Broadly spatulate with rounded apex. Margin: Entire, but slightly ruffled. Length: About 8.75 cm. Width: About 8.6 cm. Color: Upper surface: A gradual color change from 55B to 55C to 55D to 56A over time. Lower surface: A gradual color change from 55B to 55C to 55D to 56A over time. Throat or "eye": Dark red, 53A; glossy.

*Sepals.*—Appearance: Five sepals fused into a star-shaped calyx. Shape: Linear. Texture: Smooth. Color, outer surface: 146A.

*Bracts.*—Appearance: About eight fused at base. Length: About 2.75 cm. Width: About 5 mm. Shape: Linear. Color: 147A.

*Peduncles.*—Length: About 3.75 cm. Diameter: About 2.5 mm at base. Angle: Upright. Strength: Strong, flexible. Texture: Slightly pubescent. Color: Green, 146A, overlaid with dark brown, close to 200A.

*Reproductive organs.*—Androecium: Stamen number: Numerous, about 45. Stamen length: About 5 mm. Filament color: 52B. Anther size: About 1 mm by 0.5 mm. Amount of pollen: Abundant. Pollen color: 14A. Gynoecium: Pistil length: About 8.75 cm. Style color: 53A at base; becoming lighter, 52A to 52B at apex. Stigma appearance: Five, rounded. Stigma diameter: About 2 mm. Stigma color: 46A.

Disease resistance: Resistance to known Hibiscus diseases has not been observed on plants grown under commercial greenhouse conditions.

Seed production: Seed production has not been observed.

It is claimed:

1. A new and distinct Hibiscus plant named 'Candy Wind', as illustrated and described.

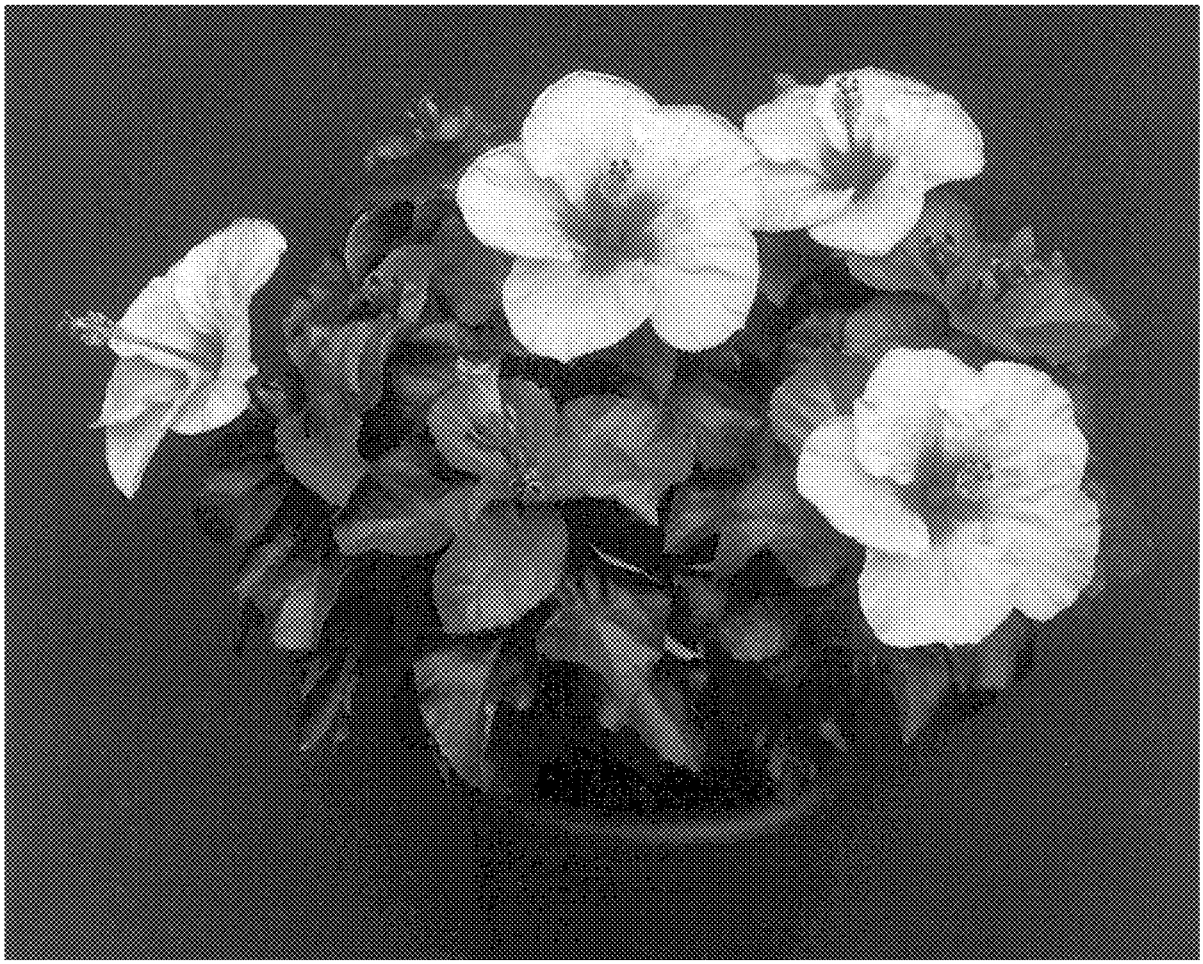

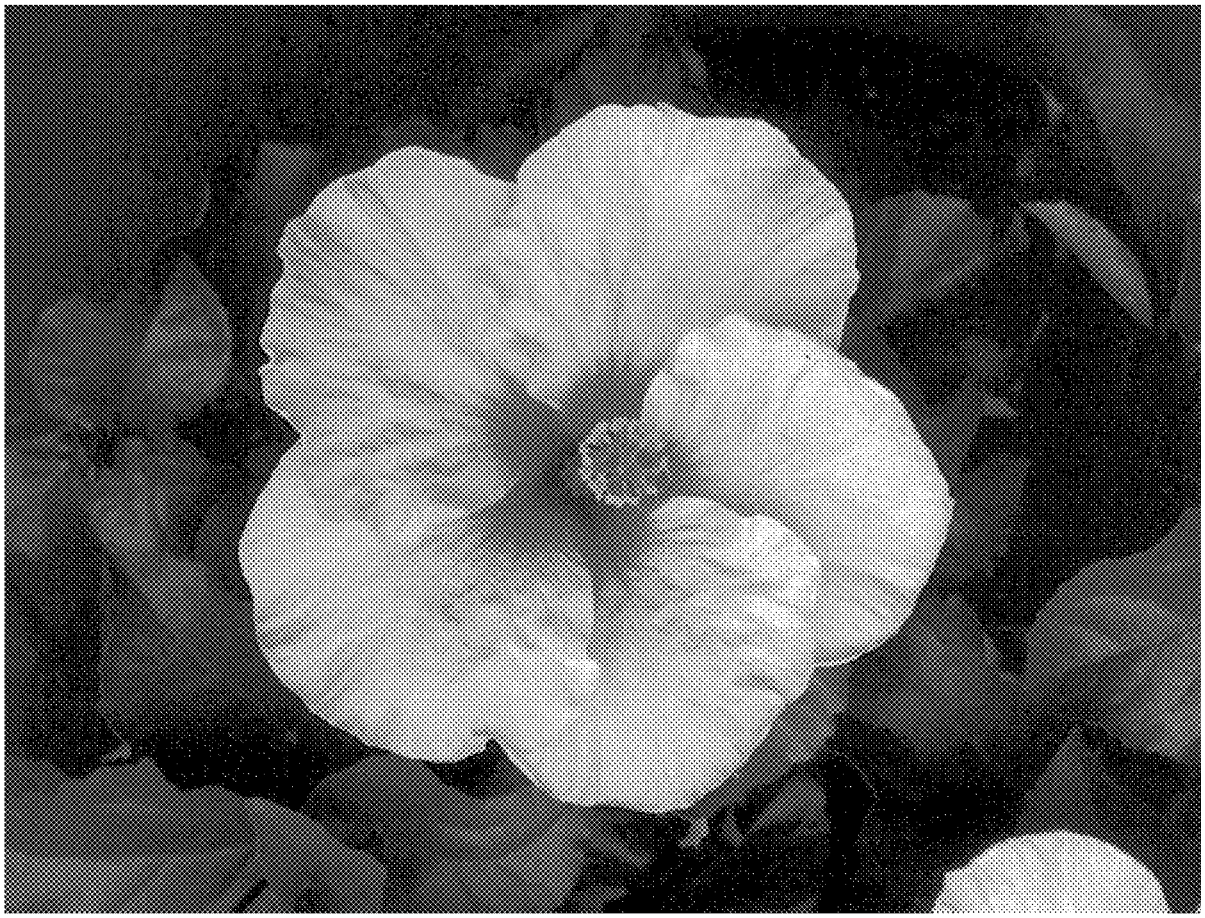

* * * * *